United States Patent [19]
van Raam et al.

[11] 4,285,140
[45] Aug. 25, 1981

[54] DEWATERING AND UPGRADING LOW RANK COAL BY A TWO-STEP HYDROTHERMAL TREATMENT

[75] Inventors: Leopold van Raam; Herman P. Ruyter; Josefus W. van Breugel, all of Amsterdam, Netherlands

[73] Assignee: Shell Oil Company, Houston, Tex.

[21] Appl. No.: 102,073

[22] Filed: Dec. 10, 1979

[30] Foreign Application Priority Data

Dec. 18, 1978 [NL] Netherlands .......................... 7812248

[51] Int. Cl.³ ................................................ F26B 5/04
[52] U.S. Cl. ........................................... 34/15; 34/12; 34/60
[58] Field of Search .......................... 34/12, 15, 60, 36

[56] References Cited

U.S. PATENT DOCUMENTS

| 3,552,031 | 1/1971 | Evans et al. | 34/9 |
| 3,992,784 | 11/1976 | Verschuur et al. | 34/15 |

FOREIGN PATENT DOCUMENTS

913531  6/1954  Fed. Rep. of Germany .

Primary Examiner—John J. Camby

[57] ABSTRACT

Low rank coal is dewatered and upgraded by heating a coal/water mixture at 150° to 300° C. at a pressure preventing water vaporization, mechanically separating the water, then heating the coal at 300° to 400° C. at a pressure allowing water vaporization.

4 Claims, 4 Drawing Figures

DEWATERING AND UPGRADING LOW RANK COAL BY A TWO-STEP HYDROTHERMAL TREATMENT

BACKGROUND OF THE INVENTION

This invention relates to a process for thermal upgrading of low rank coal, for instance brown coal and other carbonaceous material, for instance peat, lignite, wood or carbonaceous waste. In this specification such other carbonaceous material will be deemed to be included in the term "coal".

Low rank coal, in the least favorable case can contain up to 90%w water, but more generally has a water content of 40 to 70%. The water is present in various forms, namely, chemically bound, gel, and absorbed water. This water needs to be removed from the coal not only for efficient transport, but also in order to increase its calorific value (and thus its worth) and to improve its combustion properties. This water can be removed either partially by thermal drying, in which the surface and absorbed water is evaporated, or completely by thermal upgrading. In general, water removed by thermal drying will over a period of time be reabsorbed, but water removed by thermal upgrading will not, due to chemical changes which take place in the coal.

Thermal upgrading of coal can be divided into two distinct stages, namely, dewatering, and decarboxylation (removal of oxygen-containing groups). Dewatering generally takes place at about 200° C. and results in a shedding of an important part of the bound water. On separating the water from the coal, there is not a tendency for it to be reabsorbed Decarboxylation takes place at a rather higher temperature, particularly above 300° C. and results in a further structural change in the coal. The coal significantly becomes hydrophobic due to the removal of the oxygen-rich polar groups which are responsible for the hydrophilic properties of the coal. For instance, confirmation of the structural change of the coal is found from petrographic analysis, from which it is seen that the vitrinitic reflectance for a typical brown coal as a result of treatment above 300° C. has improved from ca. 0.35 before treatment to 0.70, which is equivalent to that of a subbituminous coal.

While for some types of coal thermal drying can be used with advantage, where the coal has a high water content it is less efficient in that the latent heat of vaporization of the water has to be supplied. Furthermore, there is practically no change in structure of the coal, so that the resulting dried product remains hydrophilic, and in the absence of special precautions will thus reabsorb much water in a humid environment. And, the calorific value may not be sufficiently increased to command a price which can justify the expense of transport over any considerable distance. For example, prior processes for dewatering wet, solid carbonaceous fuel materials have been described in patents such as the following: U.K. Pat. No. 844,556 describes removing water and bitumen from oil shale or peat or the like, by heating the moist material in oil, first at a temperature at which the water evaporates, then at a temperature at which the bitumen forms and evaporates. U.S. Pat. No. 3,552,031 describes heating brown coal as received from the mines at from about 100° to 300° C. at a pressure which prevents water vaporization but is less than 5000 psi, mechanically separating a fines-containing aqueous liquid which is subsequently separated into waste liquid and a sludge which is recycled into the coal to be treated. U.S. Pat. No. 3,992,784 by E. Verschuur, B. P. Ter Meulen, T. V. Herwijnen and J. Boom describes heating a slurry of brown coal and water at a temperature above 150° C. and a pressure which prevents the vaporization of water, mechanically separating this slurry into coal, water and wet fines and recycling at least some of the water to preheat the incoming coal.

SUMMARY OF THE INVENTION

The present invention relates to dewatering and upgrading a relatively low rank coal or similar carbonaceous material. A mixture of the coal and at least a substantially equal weight of free water is heated to a temperature of from about 150° to 300° C. at a pressure preventing the vaporization of the water. Substantially all of the water is then mechanically removed from the mixture. The coal is then heated for from about five minutes to five hours at a temperature of from about 300° to 400° C. at a pressure permitting the vaporization of the water so that the water content of the coal is reduced to less than about 10% by weight and the coal is significantly upgraded.

DESCRIPTION OF THE INVENTION

Figure 1:
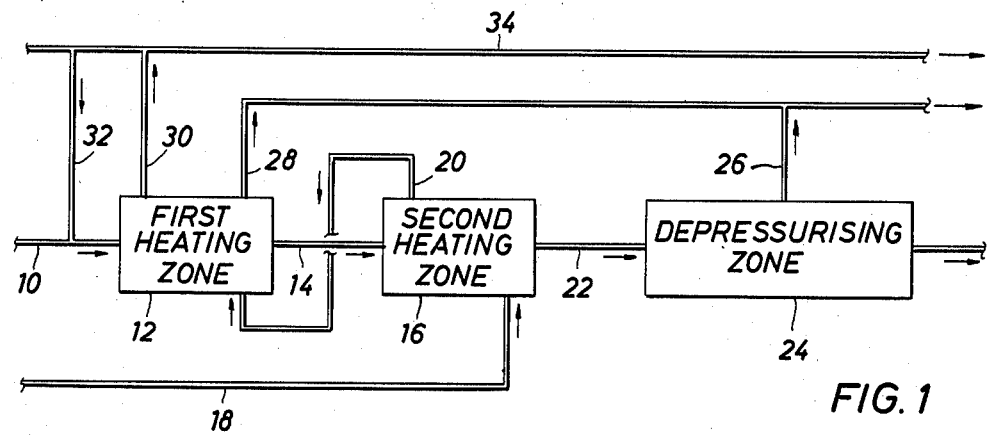
FIG. 1 is a block diagram of a process in accordance with the invention.

The present process has the considerable advantage of removing a large part of the water in the coal in the first stage at a relatively low pressure, without the need to evaporate the water, while permitting a very high degree of decarboxylation and upgrading to take place in the second stage, which can be carried out at a rather higher temperature without the inconvenience of having to maintain such a high pressure that the water does not evaporate at the temperature used in this second stage.

At present, it is not thought to be advantageous in most circumstances to exceed say 360° C., because of the gasification which starts to take place, but in a particular case should it be found to be economically attractive, in the process according to the invention, there is no technical reason why this cannot be done. In conducting the present process, substantial quantity of light tars are often released from the coal being treated. These in themselves are valuable and may be recovered from the water, or eventually specifically extracted from the coal using a solvent, such as toluene.

The present procedure of mixing the coal with a substantially equal or somewhat greater weight of water provides a significant improvement in the heat transfer properties of the material. A carbonaceous material such as a brown coal would otherwise exhibit relatively very low heat transfer property. The present procedure improves the rate at which the coal is heated during the dewatering step of the present process. It also makes it feasible to feed the coal into the heating chamber in a finely divided form such as a pumpable slurry which materially aids in the handling and pressurization of that chamber and the material carried into it.

In preferred modes of operation, at the end of the first stage of the present process, the water may be simply drained from the coal or separated by conventional mechanical means, such as by centrifuging, by agglomeration, etc. In the second stage, the coal is conveniently heated directly by a substantially dry steam, and preferably by superheated steam whose temperature may be in the range of 500° to 550° C.

The pressure under which the present process operates has been found to have a relatively small influence compared with that of the temperature, and particularly that of the pressure obtaining in the second stage. However, the pressure in the first stage should be sufficient to maintain the water in its liquid phase. For the optimum temperature range of 200° to 230° C. the pressure will be in the order of 30 to 45 bar.

Although in the first stage the dewatering takes place quite rapidly, so that apart from the time necessary to heat the coal to the dewatering temperature, no significant residence time will be required, in the second stage, the decarboxylation takes somewhat longer. Thus, depending upon the temperature and the degree of treatment to be carried out, the coal may remain at the temperature obtaining in the second stage for a period of between 5 minutes and 5 hours, though more normally between 15 and 30 minutes. It will be appreciated that the optimum residence time will normally be decided by normal cost-benefit analysis of the degree of upgrading which can be justified for a particular coal based upon and its susceptibility to the treatment.

Although water is evaporated in the second stage of the treatment, its latent heat need not be lost in the process according to the invention. It can be mostly recondensed in the first zone where the pressure is at least equal to the vapor pressure of water at the temperature obtaining there. This makes for not only improved efficiency of the process, but also increased flexibility.

The present process is suitable for treating relatively large particles including lumps in which the average largest diameters are up to about 150 millimeters or more. It is particularly suitable for treating particles in which most of the sizes are from about 20 to 150 millimeters. However, where the coal to be treated contains a significant porportion of fines which are difficult to mechanically separate from water at the end of the first stage of heating, such particles can advantageously be compressed into tablets or artificially formed lumps having sizes in the range from about 5 to 150 millimeters.

A plant or apparatus for carrying out the process according to the invention may comprise: a first reactor vessel arranged to receive a charge of coal and water and to subject it to a temperature of between 150° and 300° C. at a pressure in excess of the vapor pressure of water at the temperature used, means for separating the coal from the water, and a second reactor vessel arranged to receive coal from the first reactor vessel and to subject it to a temperature of between 300° and 400° C. at a pressure below the vapor pressure of water at the temperature used.

The first reactor vessel is conveniently provided with a feed system which is arranged to receive the coal, and to which the water required for the first stage of the treatment may be added. Alternatively, where the feed contains sufficient water a pump may be used.

In order to keep the energy requirements as low as possible, such make-up water is advantageously taken from the water extracted from the first reactor vessel. Similarly, the heat required for the first stage of the reaction may be largely supplied in the form of the steam leaving the second reactor vessel.

In one embodiment of the invention the reactor vessels are disposed one above the other, namely the first above the second, so that after equalizing the pressure in the two vessels, the charge from the first vessel can be allowed to fall by gravity into the second vessel.

In another embodiment, the charge in the first vessel, after allowing excess water to drain off, is transferred to the second vessel by mechanical means, such as an auger-like screw conveyor. Such an arrangement has the advantage that the transfer of coal from the first to the second reaction can be carried out substantially on the continuous basis.

Alternatively, the plant may comprise one or more reactor vessels, each of which is arranged to carry out both stages of the process in accordance with the invention. In its simplest form, each vessel is arranged to receive a charge of coal and water and to be heated up to a dewatering temperature between 150° C. and 300° C. at a pressure above the vapor pressure of water at the temperature used. Means are provided for separating the water from the coal (or vice versa) after the completion of the first stage of the process, and the vessel is arranged so that the coal can subsequently be heated up to a temperature between 300° C. and 400° C. at a pressure below the vapor pressure of water at the temperature used. For economy a plurality of the vessels may be arranged around a central coal feed system; they have passages for transferring water/steam from one vessel to another. The process can then be carried out batchwise, each batch remaining in a single vessel over the whole process, but steam, for example, leaving a vessel undergoing the second stage, being passed to a vessel where the first stage is in progress, and water from the first stage being used for preheating fresh untreated coal in another vessel.

The process may also be carried out continuously in a single reaction vessel. Such a vessel may comprise two zones, a first reaction zone where the first stage of the process is carried out and a second reaction zone where the second stage takes place, mechanical means being provided for progressing the coal through the vessel from the first to the second zone. The vessel may conveniently be inclined, so that the water tends to remain in the lower zone, which is in effect the lower temperature zone. High-temperature steam entering the upper zone is arranged to flow towards the lower zone in countercurrent to the coals whose temperature rises as it is progressed upwardly through the reaction vessel.

In this way an optimum use of the energy input is made, the steam being mostly condensed by the time it reaches the lower end of the first reaction zone, and any water evaporated from the coal in the upper part of the reactor is recondensed lower down, so that its latent heat of vaporization is not lost.

The mechanical means may comprise a conveyor having a screen, buckets or arms, which move either continuously or intermittently, or which reciprocate quickly or slowly. In a preferred embodiment the conveyor comprises a plurality of foldable buckets, arms or fork-like elements attached to a central drive which, during an upward stroke, entrain the coal to move it upwardly from an original position A by an element a to a new position B. During a reverse stroke, the elements fold towards the drive and the element a returns to its original position A leaving the coal at B. An element b is then ready on the next upward movement to entrain coal at B to progress it to a new position C above B, and so on. Such a reciprocating conveyor has the advantage that it can progress the coal slowly through the reactor vessel, while ensuring some gentle mixing of the coal without causing it to be broken up. The drive may be effected hydraulically, so that no complicated seal has to be provided between the inside and the outside of the vessel, due to the pressure obtaining in the vessel. Alternatively, a screw conveyor may be used.

The reactor vessel itself may be constructed as an inclined tubular steel vessel with or without insulation, or alternatively may comprise a reinforced concrete vessel of any desired cross section (which is not necessarily constant over its length) not only better to accommodate the conveyor, but also to facilitate the draining of water from the coal.

At the outlet of the second zone, the treated coal may conveniently be discharged through an extruder, and regranulated, or allowed to remain in lumps held mainly together by their own tar content, as required.

Particularly where the upgrading treatment is severe, there will be some valuable coal tar-like products released; these may be removed with the water and separated from it by conventional means, in solvent extracted from the treated coal.

In FIG. 1 a mixture comprising low rank coal and 40 to 50%w water enters by line 10 a first zone 12, where its temperature is increased to between 200° and 250° C. at a pressure of 30 to 45 bar. Under these conditions, the pressure exceeds the vapor pressure of the water present, so that the water remains in the liquid phase. At the end of the required residence time, which will depend upon the characteristics and the age of the coal and its grading and the temperature employed, the coal leaves the first zone 12 by line 14 and passes to a second zone 16. At this stage the coal has already been partially upgraded and will have lost approximately three quarters of its initial water content, and being somewhat less hydrophilic, can be passed to the second zone 16 with little water.

While in the second zone 16 the pressure is substantially the same as that obtaining in the first zone, the temperature is substantially higher, namely 320° to 350° C. At this temperature and pressure the water will be in the vapor phase, and during the treatment in the second zone any remaining surface water will be quickly evaporated, bonded water will be liberated and likewise evaporated, and the polar oxygen groups will be mainly converted to $CO_2$.

Heat is supplied to the second zone in the form of superheated steam at 500° C. to 550° C. via line 18, which steam is conducted by means of line 20 to the first zone 12.

On leaving the second zone by line 22 the treated coal is depressurized at 24 and any gases and remaining steam are removed by line 26. Normally these gases will contain water vapor, some $H_2S$ and traces of other gases, such as light hydrocarbons and a substantial proportion of $CO_2$, generated in the second zone due to the decarboxylation which takes place there. Some gas is also drawn off from the first zone at 28; and where these gases are sufficiently rich in hydrocarbons, these can conveniently be used partly or wholly to supply the heat required for carrying out the process which is slightly endothermic.

Water is drawn off from the first zone at 30, in order to keep the ratio of water to coal within the desired limits; normally about 1 part water to 1 part coal. The water is found to be necessary not only for the upgrading process to take place, but also to ensure effective and efficient heat transfer to the coal. This water, which is nominally at 200° to 250° C., can be recirculated via line 32 to the line 10 to form a slurry of the coal to be processed, or its heat can be transferred (not shown) to the pressurized feed in the line 10. Effluent water leaves by line 34 and will need to be treated before disposal in order to remove contaminants, which may include mineral matter, dissolved sulphurs, etc., and eventually to reduce its temperature.

Treated coal from the process typically is shiny, hard and, having a water content down to below 5%w, is hydrophobic, due to the removal of the majority of its polar oxygen groups during the treatment.

In certain instances the treated coal is coated with its own tar, or can be directly binderless-briquetted using its own tar content. Alternatively, it can be further processed, gasified, etc. as required.

A particularly notable parameter in the process is the temperature, and particularly that in the second zone. For example, an increase from 300° C. to 340° C. can reduce the residence time by an order of magnitude to achieve the same increase in calorific value of the treated coal. There is a limit as to how far the temperature in the second zone can be increased, due to the onset of rapid gasification of the coal, which tends to take place from about 400° C., which limits the temperature at which the superheated steam may enter to about 500°–550° C.

Figure 2:
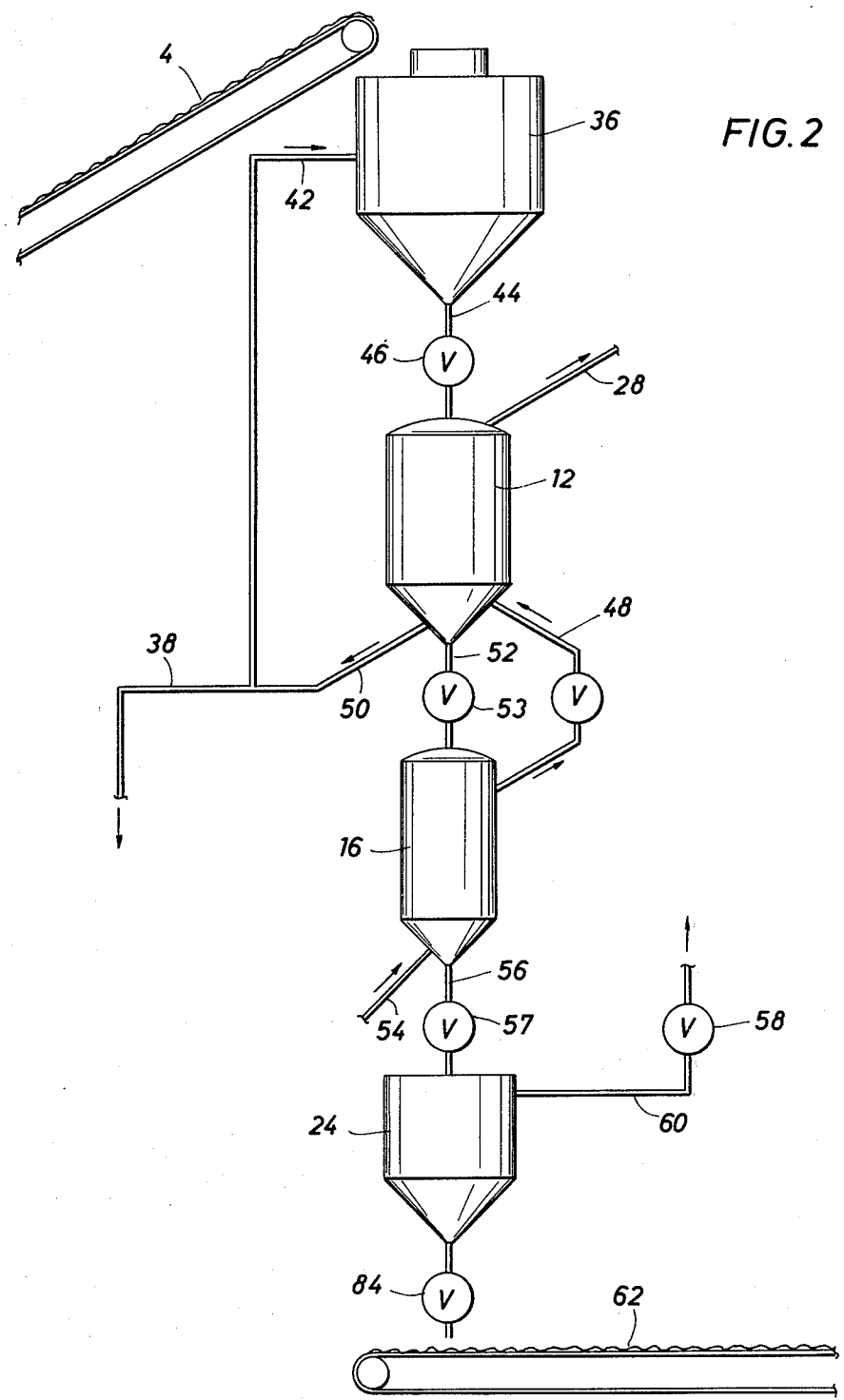
FIG. 2 is a schematic diagram of a plant in accordance with the invention for carrying out the process described with reference to FIG. 1, as a batch process.

Turning to FIG. 2, coal is passed sequentially through four vessels 36, 12, 16, 24, to effect the upgrading process in accordance with the invention.

A measured quantity of coal particles, which are mostly between 20 and 150 mm, are fed into an upper lock hopper vessel 36 by means of a conveyor 40 and water is added through line 42 to increase the free water content of the mixture to 60%w of the total (i.e., 40%w coal).

When the first reactor vessel 12 is empty, the prepared charge in the upper lock hopper vessel 36 is discharged into the vessel 12 through a communicating passage 44, which is closed by valve 46 after the discharge has taken place. Superheated steam enters via line 48 at 35 bar at between 315° and 350° C., and is blown through the mixture until its temperature reaches 230° C. at 45 bar. Any gases and uncondensed steam are removed by line 28.

Depending upon the type of coal, these conditions are held long enough substantially to complete the first stage of the dewatering of the coal. The water is then allowed to drain from the vessel via line 50, whence it is partly recirculated to the new charge in the upper lock hopper vessel 36 and partly discharged as effluent via line 38 for suitable treatment and heat exchange. For a typical sample of Victorian Brown Coal for an initial charge of 40 kg coal + 60 kg water, 40 kg water will be removed after the treatment in vessel 12.

The remaining 60 kg moist coal is then discharged into the second reactor vessel 16 through a communicating passage 52 between the two vessels. After discharge the passage is closed by valve 53 and superheated steam at 540° C. and 45 bar enters the vessel at 54, and is blown through the semi-dewatered coal until its temperature has attained 340° C. The cooler, but still superheated, steam leaves the second reaction vessel 16 by the line 48 leading to the first reactor vessel 12 as mentioned above.

When the charge in the second reaction vessel 16 has reached the predetermined temperature, the steam supply is stopped and its discharge may take place to a lower lock hopper vessel 24 through a communicating passage 56. When the discharge is complete, the passage 56 is closed by valve 57 and the pressure in the vessel 24 is reduced by opening a valve 58 in a vent line 60.

Under the conditions mentioned above approximately 96%w of the gas procured will generally comprise $CO_2$; traces of $H_2S$ and light hydrocarbons will also be present. In the cited example, about 40 kg coal having a final water content of under 10%w will be recovered. Approximately 17 kg $H_2O$ and 3 kg $O_2$ are removed from the coal in the second vessel. Of the coal approximately 5.5 kg will be recovered in the form of light tars, the remainder as hard, shiny black or dark brown lumps, they can be directly briquetted without the addition of a binder.

After degassing and cooling, the treated coal particles are dosed from the vessel 24 onto a delivery conveyor 62.

Such a batch process has the advantage that it is very flexible, so that different qualities of coal can be treated under optimum conditions both of temperature and residence time. Furthermore, it has the advantage of requiring only relatively simple equipment. The results achieved using a process in accordance with the invention are comparable with those obtainable to date using only sophisticated, very high pressure equipment.

Figure 3:
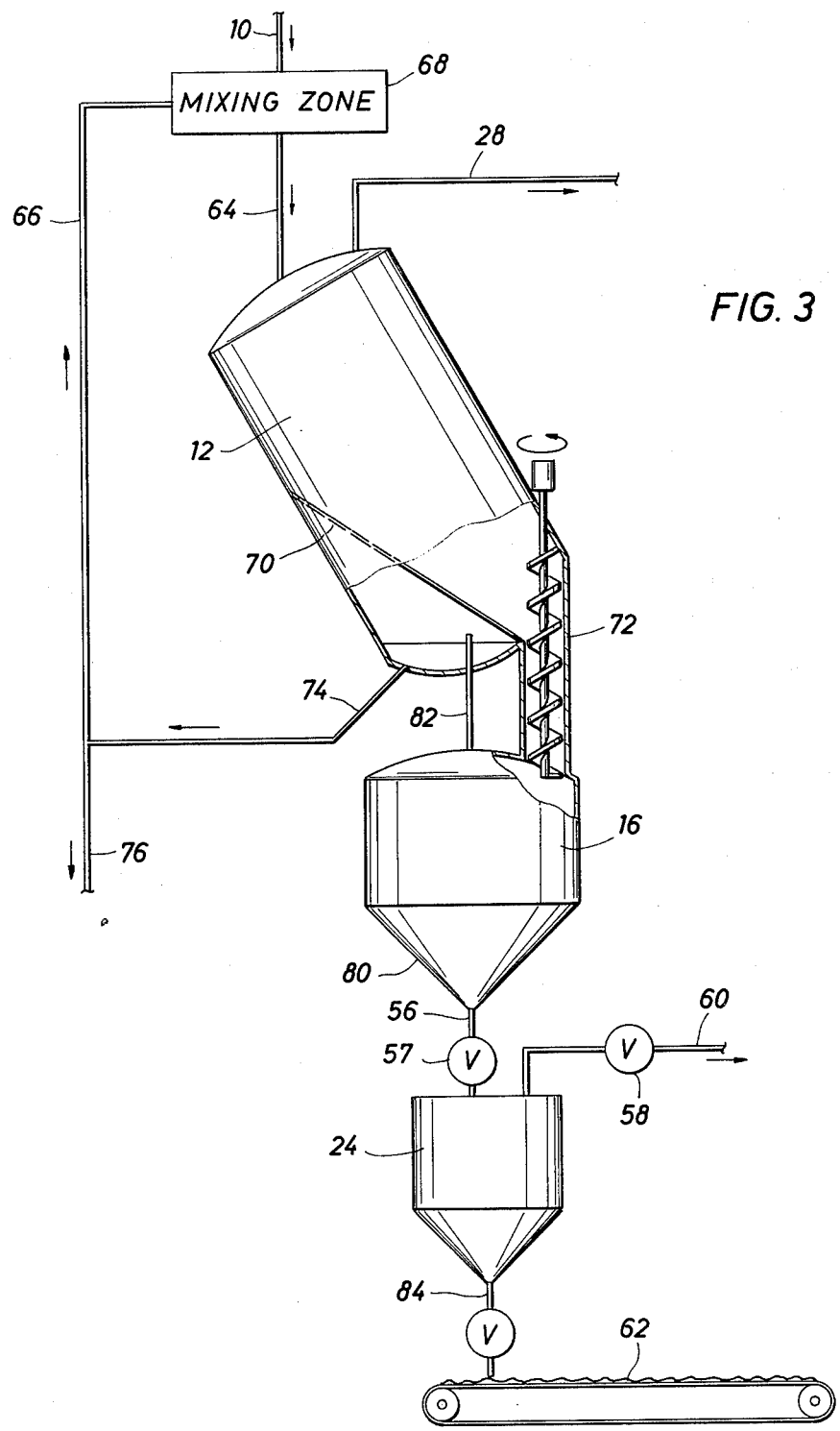
FIG. 3 is a schematic diagram of a plant in accordance with the invention for carrying out the process described with reference to FIG. 1 as a semi-continuous process.

The plant shown in FIG. 3 is a modified version of that shown in FIG. 2, but has the advantage that it is adapted for semi-continuous operation.

The first reactor vessel 12 is fed by line 64 with a slurry of coal particles of approximately 5 mm in water under pressure, and already at an elevated temperature, due to the use of hot process water via line 66 to make up the slurry at 68. As before, steam at 315°–350° C. is used to heat the slurry to some 220° C. at 30 to 35 bar. The coal particles slowly move down the vessel and water is drained off through a screen 70, while the coal particles are entrained by a screw conveyor 72 leading to the second reactor vessel 16.

The water is evacuated from the bottom of the first reactor vessel through line 74 and some of it, as before, is reused to make up the slurry via the line 66. The remainder is discharged via line 76 after treatment and heat exchange. The spent steam which leaves the first reactor vessel 12 by line 78 can also be used to heat the water or the slurry intake.

The second reaction vessel 16, which is smaller than the first reaction vessel 12, is provided with a steam inlet 80, which permits superheated steam at 540° C. and 40 bar to be blown through the partly dewatered coal particles. Some of the remaining water will of course be evaporated and will pass with the steam to the first reactor vessel via a line 82, but due to the conditions obtaining in the latter much of the water will be recondensed and thus its latent heat will not be lost.

The contents of the second reactor vessel 16 are intermittently released to a lock hopper vessel 24 through a closeable communicating passage 56. The pressure in the lock hopper vessel 24 is reduced by removing the gas produced by the coal through a line 60. The coal is then discharged through the outlet 84 of the hopper onto a conveyor 62.

In the event that the upgraded coal is to be used directly for gasification, briquetting, or required for further processing, the outlet from the lock hopper vessel can be modified appropriately, in order to benefit from the temperature and/or pressure of the charge.

Figure 4:
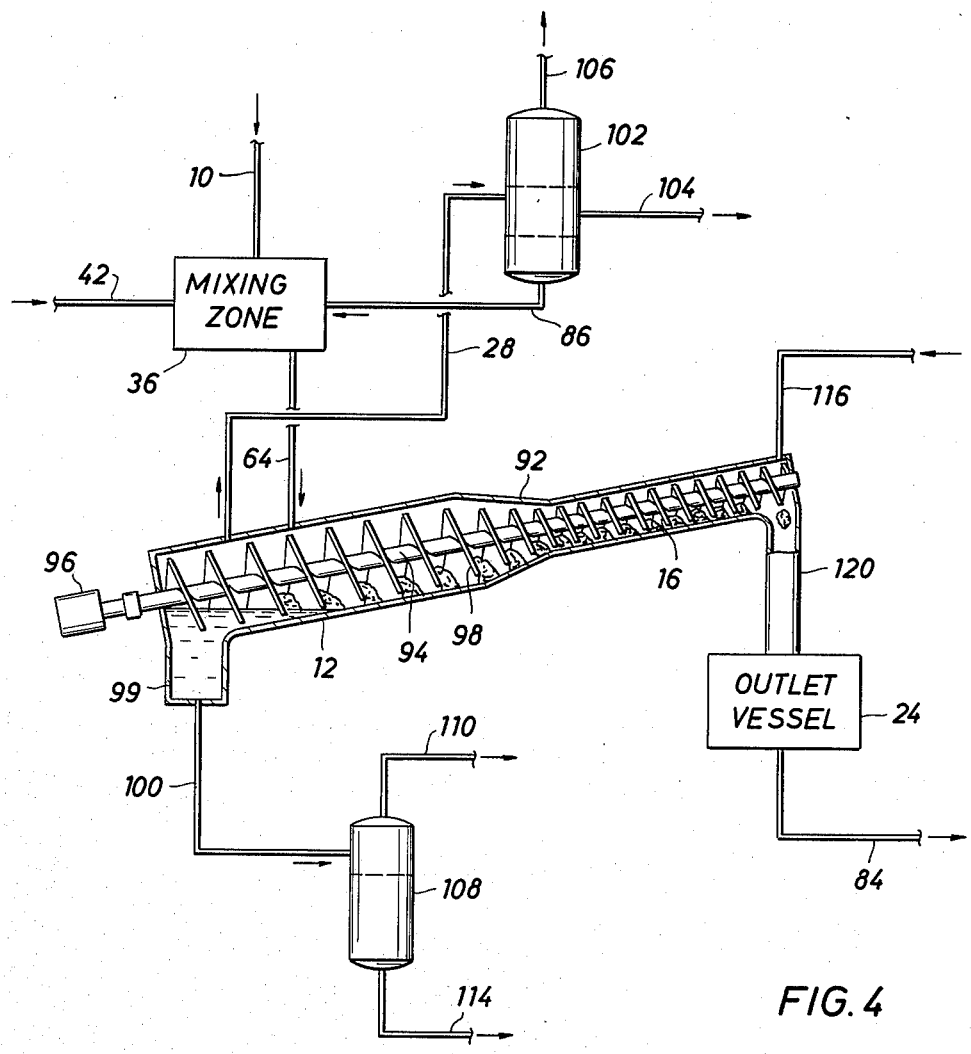
FIG. 4 is a schematic diagram of a plant in accordance with the invention for carrying out the process described with reference to FIG. 1 as a continuous process.

The plant shown in FIG. 4 is arranged for continuous operation and is suitable where large quantities of coal are to be treated. As with the plant shown in FIG. 2, it comprises essentially an inlet vessel 36, a reactor vessel 88, which is effectively divided into a first reaction zone 12 for carrying out the dewatering step, and a second reaction zone 16 for the decarboxylation, and an outlet vessel 24.

Coal is supplied to the inlet vessel 36 and water may be added to it via lines 42 and 86. It then passes to the first reaction zone 12 of the reactor vessel 88.

The reactor vessel 88 comprises an elongated, cylindrical vessel whose two reaction zones 12, 16 are of different diameters and are connected by a conical portion 92; the first reaction zone 12, being of a larger diameter than that of the second 16. The axis of the vessel 88 slopes upwardly from the first zone 12 to the second zone 16 at an angle which is generally between 5° and 15°; here the angle is approximately 12½°. In operation the coal is progressed through the vessel 88 by an archimedian-type screw conveyor 94 driven by a motor 96 situated externally.

The first zone 12 of the vessel 88, apart from the coal, is substantially filled with water at 240° C. and a pressure of 45 bar is maintained in the vessel. Coal fed to it from the inlet vessel 36 to enter via line 64. The screw conveyor 94 entrains the coal and progresses it slowly to the second zone 16 via the conical portion 92. The water remains mainly in the first zone. Excess water collects in a sump 99, whence it is removed through line 100 and transported to a settling tank 108.

After settling out in vessel 108 the water can be separated from light tar formed from the coal. The tar is removed via line 110, the water via line 114. The water may be recirculated to the coal in the inlet vessel 36 via line 42 as mentioned above. Any gases and uncondensed steam are removed from the vessel 88 via line 28 to a coalescer 102, whence water, light tars and gases are removed through lines 86, 104 and 106 respectively.

Due to the slope of the reactor vessel and the fact that the lightly compacted coal only partly fills the screw conveyor 94, permitting the counter flow of steam from the second reactor zone 16 to the first, the majority of the water tends to remain in the first zone 12, while the coal is progressed upwardly from the first zone to the second.

The steam enters the second zone 16 at 116 superheated to 540° C. The pressure in the second zone is substantially that obtaining in the first zone, namely, 45 bar, and thus, as in the other instances described above, any water remaining with the coal is quickly flashed off. The coal is heated by the steam to approximately 340° C., at which temperature it remains for the desired residence time before being discharged through a vertical passage 120 to the outlet vessel 24. Any gases given off by the coal are vented and the upgraded coal, after cooling, is ready for transport or for further treatment as required, for example, a solvent extraction step for removing light tars produced during the upgrading process.

As mentioned above, the coal may be fed to the reactor vessel in the form of a slurry, or by means of a lock-hopper system as described with reference to FIG. 2. It may also be fed to the reactor by means of a solids pump or screw mechanism, and the box indicated by 36 may represent any appropriate feed mechanism. Similarly, at the outlet, the treated coal may be discharged via a lock-hopper system as described with respect to FIG. 2, or by a screw mechanism followed by a granulator, for example.

Where the carbonaceous material to be treated includes fines in a proportion which tends to interfere with the mechanical separation of water from the carbonaceous material after the first heating step, the so-heated carbonaceous material can advantageously be compressed into tablets having largest dimensions in the range of from about 5 to 100 mm by compaction or extrusion. In that connection, the term "tablets" is used to refer to artificially formed lumps or regular or irregular size such as briquettes, extrudates and the like, such compacted masses being formed, for example, by a solids pump.

The optimum tablets are formed by briquetting due to their consistent form and standard shape, but these may be difficult to make where the coal has a high water content. More simply manufactured are tablets formed by extrusion where they are in the form of a broken string of coal. Where necessary, the extruded string may be cut to a desired length rather than being allowed to break at random. Alternatively, the tablets may be in the form of compacted masses formed by a solids pump.

Where the raw or first stage-treated coal does not have sufficient self coherence, for example, due to the absence of self-contained tars, a hydrocarbon binder such as bitumen or a short residue may conveniently be added.

The use of a binder may prove particularly useful in that it may permit an even greater proportion of the smaller particles and fines to be compacted due to their affinity for the hydrocarbon binders that are generally used. Although the binder may have a higher value than the coal, its use may be justified by the increased recovery of the coal; in addition by taking its calorific value into account in assessing the final value of the upgraded coal, the overall net increase is likely to be favorable.

In fact, much of any binder used may be recovered with the tar released by the coal during subsequent heat treatment. Where the binder has a relatively high sulphur content, the water soluble sulphur compounds may be leached out during heat treatment, which may actually result in an increase in value of the binder.

The binder may be added in powdered, liquefied or emulsified form.

While in general the compaction will take place with the coal in its cold, moist condition, there are definite advantages to be gained from carrying out the process on the preheated moist coal, possibly even after the first stage of the heat treatment. The principal advantage is that during heating the tars contained in the coal soften and aid significantly the effective compaction of the coal and that the compaction tends to squeeze the water more effectively out of the coal.

The pressure used for compaction or compression of the coal will depend very largely upon the type of coal in question, but as a rule the pressure chosen will normally fall within the range 1 to 25 $kN/cm^2$ and preferably in the range 5 to 15 $kN/cm^2$. Typical results after heat treatment to 340° C. show a volume reduction of the brown coal of not less than 40% and a reduction of its water content of at least 60%.

The means for compacting the coal may conveniently comprise a briquetting press, an extruder or a solids pump. This may advantageously be arranged to introduce the coal into a heat treatment zone under pressure. The choice of the compaction means will also depend upon the desired form of the product, and has the advantage that this can be chosen to suit the situation.

EXAMPLES

1. A sample of Victoria brown coal was compacted at a pressure of 5 $kN/cm^2$, to form tablets of 11.4 mm diameter. The tablets were subjected to a temperature of 257° C. at 45 bar for 60 min. They were then heated at 359° C. at 40 bar for a further 60 min.

The untreated coal contained 1.17 kg water/kg dry coal and had a calorific value of 6680 cal/g dry coal. The treated coal contained 0.0 kg water/kg dry coal and had a calorific value of 7600 cal/g dry coal. During the treatment there was a crimping of 63% and the product volume was 37% of the original volume, the final diameter of the tablets being 8.2 mm. There was a weight loss of 30% based on the dry coal input.

2. A sample of Victoria brown coal was compacted at a pressure of 15 $kN/cm^2$ to form tablets of 11.4 mm diameter. The tablets were subjected to a temperature of 250° C. at a pressure of 50 bar for 1 hour. They were then heated to 320° C. for a further hour.

The untreated coal contained 1.16 kg water/kg dry coal and the results were substantially identical to those set out in Example 1.

3. A sample of Morwell brown coal was compacted at a pressure of 5 $kN/cm^2$ to form uniform tablets. The tablets were subjected to a temperature of 340° C. at a pressure of 150 bar for 1 minute.

The untreated coal contained 1.58 kg water/kg dry coal and had a calorific value of 6700 cal/g dry coal. The treated coal contained 0.53 kg water/kg dry coal and had a calorific value of 7600 cal/g dry coal. During the treatment there was a crimping of 40% and the product occupied 60% of its original volume. There was a weight loss of approximately 10% based on the dry coal input.

What is claimed is:

1. A process for dewatering and upgrading low rank coal or other carbonaceous material comprising:
    heating a mixture of the coal and a substantially equal weight of free water to a temperature of from about 150° to 300° C. while maintaining a pressure which substantially prevents the vaporization of water;
    mechanically separating substantially all of the water from the mixture; and
    heating the so-separated coal for from about 5 minutes to 5 hours at a temperature of from about 300° to 400° C., which temperature exceeds the temperature used in the prior heating step, is applied at a pressure which at least substantially equals the pressure used in the prior heating step and is a pressure at which water is vaporized so that the water content of the coal is reduced to less than about 10% by weight and the coal is significantly upgraded by decarboxylation without significant gasification.

2. The process of claim 1 in which each of said heating steps is effected by contacting the material to be heated with a substantially superheated steam.

3. A process for dewatering and upgrading low rank coal or other carbonaceous material comprising:

heating a mixture of the coal and a substantially equal weight of free water to a temperature of from about 150° to 300° C. while maintaining a pressure which substantially prevents the vaporization of water;

compressing the so-heated coal into tablets having maximum diameters of from about 5 to 100 mm;

mechanically separating substantially all of the water from the mixture;

heating the so-separated coal for from about 5 minutes to 5 hours at a temperature of from about 300° to 400° C. and a pressure at which water is vaporized so that the water content of the coal is reduced to less than about 10% by weight and the coal is significantly upgraded by decarboxylation without significant gasification.

4. The process of claim 3 in which a tar is solvent extracted from the water which is mechanically separated following the first heating step.

* * * * *